(12) United States Patent
Klimant

(10) Patent No.: US 6,602,716 B1
(45) Date of Patent: Aug. 5, 2003

(54) METHOD AND DEVICE FOR REFERENCING FLUORESCENCE INTENSITY SIGNALS

(75) Inventor: Ingo Klimant, Regensburg (DE)

(73) Assignee: PreSens Precision Sensing GmbH, Neuburg (DE)

( * ) Notice: Subject to any disclaimer, the term of this patent is extended or adjusted under 35 U.S.C. 154(b) by 0 days.

(21) Appl. No.: 09/463,394

(22) PCT Filed: Jul. 30, 1998

(86) PCT No.: PCT/EP98/04779

§ 371 (c)(1),
(2), (4) Date: Apr. 10, 2000

(87) PCT Pub. No.: WO99/06821

PCT Pub. Date: Feb. 11, 1999

(30) Foreign Application Priority Data

Aug. 1, 1997 (DE) .......................................... 197 33 341
Jul. 2, 1998 (DE) .......................................... 198 29 657

(51) Int. Cl.$^7$ ...................... G01N 33/53; G01N 33/543; G01N 21/76; G01N 21/00; G01J 3/00
(52) U.S. Cl. ............................. 436/172; 436/8; 436/57; 436/63; 436/164; 436/171; 436/518; 436/524; 436/528; 436/800; 436/805; 436/823; 435/4; 435/7.1; 435/7.72; 435/7.9; 435/7.92; 435/174; 435/175; 435/176; 435/177; 435/178; 435/808; 435/973; 422/52; 422/55; 422/68.1; 422/71; 422/82.05; 422/82.07; 422/82.08; 422/82.11; 250/200; 250/231.16; 250/216; 250/330; 250/493.1; 356/51; 356/73; 356/73.1; 356/398; 356/433; 356/444; 356/625; 356/629; 356/639; 356/640; 356/904; 356/925; 356/928
(58) Field of Search ........................... 250/231.16, 200, 250/216, 330, 493.1; 356/51, 73, 73.1, 625, 629, 639, 640, 398, 433, 444, 904, 925, 928; 422/52, 55, 68.1, 71, 82.05, 82.07, 82.08, 82.11; 435/4, 7.1, 7.72, 7.9, 7.92, 287.1, 288.7, 808, 973, 174–182; 436/518–535, 8, 57, 63, 164, 171, 172, 800, 805, 823

(56) References Cited

U.S. PATENT DOCUMENTS

| | | | |
|---|---|---|---|
| 5,102,625 A | 4/1992 | Milo | 422/82.07 |
| 5,264,847 A | 11/1993 | Bhandari | 341/81 |
| 5,485,530 A | 1/1996 | Lakowicz et al. | 382/191 |
| 5,580,749 A | 12/1996 | Hughes | 435/29 |
| 5,618,732 A | 4/1997 | Pease | 436/8 |
| 5,632,958 A | 5/1997 | Kane et al. | 422/82.07 |
| 6,251,581 B1 * | 6/2001 | Ullman et al. | 252/582 |
| 6,340,599 B1 * | 1/2002 | Singh et al. | 252/301.16 |
| 6,406,913 B1 * | 6/2002 | Ullman et al. | 252/700 |
| 6,466,310 B2 * | 10/2002 | Nguyen et al. | 356/73.1 |

FOREIGN PATENT DOCUMENTS

| | | |
|---|---|---|
| AT | 399 229 | 8/1994 |
| DE | 19548922 | 7/1997 |
| EP | 0 354 204 | 2/1990 |
| EP | 0 597 566 | 5/1994 |
| FR | 2522150 | 8/1983 |
| WO | 92 04618 | 3/1992 |
| WO | 95 10766 | 4/1995 |
| WO | 97 10495 | 3/1997 |

* cited by examiner

Primary Examiner—Long V. Le
Assistant Examiner—Kartic Padmanabhan
(74) Attorney, Agent, or Firm—Rothwell, Figg, Ernst & Manbeck

(57) ABSTRACT

A method and device for fluorimetric determination of a biological, chemical or physical parameter of a sample utilize at least two different luminescent materials, the first of which is sensitive to the parameter, at least with respect to luminescence intensity, and the second of which is insensitive to the parameter, at least with respect to luminescence intensity and decay time. The luminescent materials have different decay times. The time- or phase behaviour of the resulting luminescence response is used to form a reference value for determination of a parameter.

14 Claims, 5 Drawing Sheets

1

2

3

4

METHOD AND DEVICE FOR REFERENCING FLUORESCENCE INTENSITY SIGNALS

CROSS-REFERENCES TO RELATED APPLICATIONS

This application is 371 of PCT/EP98/04779 filed Jul. 30, 1998.

BACKGROUND OF THE INVENTION (1) Field of the Invention

The invention relates to a method and device for use with a spectrophotometer, for fluorimetric determination of a biological, chemical or physical parameter of a sample, utilizing at least two different luminescent materials, the first of which is sensitive to the parameter at least with respect to luminescence intensity, and the second of which is insensitive to the parameter at least with respect to luminescence intensity and decay time.

The invention relates in particular to a new principle of optical detection of chemical parameters with the use of optical sensors, based on phase shift- and time-resolved measurements. The modulation frequencies used are between 0.5 and 5 MHz and may be detected with the use of low-cost optical semiconductor components.

(2) Description of the Related Art

As is known from the literature and practical experience with optical sensors, determining decay time instead of intensity as a measurement variable has certain practical advantages in luminescence measurements. Fluctuations in the optical system, for instance, will hardly or not at all interfere with decay time. Neither changes in intensity of the light source and sensitivity of the photodetector nor signal losses due to bent fibers or influences on signal intensity by changes in the sensor geometry will have any effects on the measured signal. This will also apply to undefined optical properties of the sample (such as turbidity, intrinsic colour, or refractive index), which could cause problems in intensity measurements.

Further, in many cases the measured signal is largely independent of the concentration of the indicator in the sensitive layer. For this reason a slight degree of photodecomposition or leaching is less critical.

In the literature a large number of measuring principles have been proposed for monitoring chemical parameters by means of decay time. One of the most frequently used methods is dynamic luminescence quenching, i.e., non-radiative deactivation of the excited state of a luminescence indicator by the analyte. This approach is used for optical detection of molecular oxygen and the detection of halide and heavy metal ions (1).

A further method of deactivation utilizes photo-induced electron transfer in a single indicator molecule. In this instance (shortly called PET) the luminescence indicator is included in different forms, only one of which (i.e., acid form or with bonded metal ion) features strong luminescence and long lifetime. In the other form (i.e., basic form or without bonded metal ion) the indicator has a free electron pair, which can deactivate the excited state without radiation. As a consequence, both decay time and luminescence quantum efficiency will decrease. This principle may be employed with optical pH measurement, or optical ionic sensor technology (2).

Another proposed method of decay time measurement utilizes the effect that certain pH indicators exhibit different luminescence intensities and different, though defined, decay times for their protonated and deprotonated states. Such indicators include derivatives of seminaphthofluorescein, for example. In such instance luminescence of the acid and basic form is monitored simultaneously. The respective (pH-dependent) ratio of the two intensities will yield a mean decay time which can be measured (3). A precondition for this method is that both forms of an indicator are luminescent, and that their absorption and emission spectra show significant overlap.

It should be noted that in most of the measuring principles cited above, measured decay times are in the range of a few nanoseconds as a rule. Accurate measurements of decay times in the lower nanosecond region necessitate expensive instrumentation, however, as they require not only very fast circuitry and high modulation frequencies but also fast light sources and detectors. It seems unlikely for this reason that low-cost instruments utilizing optical semiconductor components, such as light emission diodes and photodiodes, will be developed for this type of sensors in the near future. If optical sensors are to be used for a wide range of applications, however, inexpensive instrumentation is indispensable. For this reason there is considerable interest in decay time sensors whose measuring range is in the microsecond or even millisecond region. So far such sensors have been developed and put to practical use almost exclusively for optical oxygen measurement, where indicators with decay times of up to several milliseconds are employed.

A recent approach to develop new, long-life decay time sensors makes use of radiationless energy transfer from a luminescent donor molecule, whose photophysical properties are not affected by the analyte, to a dye indicator referred to as acceptor, which is sensitive to the analyte. Depending on the respective analyte concentration the absorption spectrum of the acceptor must overlap to a varying extent with the emission spectrum of the donor. Suitable luminescent donors are transition metal complexes with ruthenium(II), ruthenium(I), or osmium and iridium as central atom. These compounds feature long lifetimes (some 100 nsec to a few microseconds) and high quantum yields. This novel approach was first proposed by Lakowicz and has recently been employed with optical pH sensors. In principle, such optodes could be put to use for $pCO_2$, $NH_3$, and ion detection in a similar manner (4,5).

One serious problem with the practical use of such sensors arises from the fact that the rate of energy transfer, and hence measurable mean decay time will significantly depend not only on the distance and positioning of donor and acceptor molecule, but also on the concentration of the acceptor in the matrix. As a consequence, each change in distribution and distance of the indicators in the matrix will lead to changes in the sensor characteristic. Swelling of the matrix, in particular, will constitute a grave problem.

Another problem is caused by the influence of oxygen on the sensors. Since the luminescence of the long-life donors used often is substantially quenched by oxygen, oxygen concentration must be included in the measurement and the measured signal must be corrected. In addition, reactive singlet oxygen is produced during this process in the membrane, which will accelerate photo-decomposition of the immobilized indicators, thus reducing both storage and long-term stability. As a consequence, one of the classical advantages of decay time measurement is lost.

A device of the above described type is disclosed in U.S. Pat. No. 5,102,625, where the intensities of two luminescent materials are separately measured by means of two separate measuring channels. The intensity ratio of the two luminescent materials is used as the final signal for monitoring of the parameter. The luminescence decay times do not enter the measurement. The two luminescent materials have differing spectral regions.

BRIEF SUMMARY OF THE INVENTION

It is an object of the present invention to propose a method and device for fluorimetric determination of the parameter of a sample, which combine high measuring accuracy and comparative simplicity of instrumentation.

The invention describes a new measuring principle permitting fluorimetric determination of various chemical, physical, and biological parameters with the use of time-resolved methods and phase modulation techniques. The invention permits effective referencing of the intensity signals of the majority of fluorescence.sensors described in the literature by admixing a long-life luminescent material. For this purpose two different luminescent materials are jointly co-immobilized in the sensor. The sum signal is derived from a luminescence signal with constant long-life decay time (at least some hundred nanoseconds) and a short-lived fluorescence signal. Whereas the parameters of long-lived luminescence are not affected by the analyte, the intensity of the co-immobilized, short-life luminescent material will vary with the respective analyte concentration. As the phase shift $\phi_m$ obtained by phase modulation techniques depends exclusively on the ratio of the partial intensities of the two individual luminescent materials, this parameter will directly reflect the intensity of the luminescent material sensitive to the parameter. The invention thus is concerned with a new method of internally referencing the signal intensity of fluorophores without the necessity of a second light source or a second photodetector. Provided that the distribution of the two luminescent materials is maintained constant during manufacture, $\phi_m$ will depend exclusively on the physical or chemical parameter being monitored, whilst variations in the optoelectronic system, in losses in the fiber optics and in the optical properties of the sample will have no influence on the signal.

DETAILED DESCRIPTION OF THE INVENTION

Preferably, both luminescent materials will absorb light in the same range of wavelengths, which will enable them to be excited into luminescence by means of a single light source. Emission spectra will preferably be in the same spectral region. It will be possible, for example, to excite both luminescent materials with blue light at a wavelength of 450 nm, one luminescent material emitting green light at 520 nm and the other one red light at 600 nm, as both signals can still be measured with one and the same detector. It will also be possible, however, to simultaneously measure the luminescence of two luminescent materials whose emission spectra differ from each other significantly.

The measuring method described has the advantage that the long-life luminescent material need not exhibit analyte-specific response but solely acts as carrier of a constant background signal with long decay time, which is modulated by the short-life luminescent material. For this reason a large number of phosphorescent compounds described in the literature are suitable for this purpose.

The long-life luminescent material need not interact with sample, analyte, or fluorescence indicator, and can thus be immobilized such that it is inert to all sample components, which will exclude a priori any potential interference by chemical parameters.

Following is a more detailed description of the invention by means of examples.

FIG. 1 shows the dependence of the measured phase angle $\phi_m$ on the relationship between intensity of the fluorescence indicator and the reference luminescent material; A strong fluorescence signal, B weak fluorescence signal. Labels used are flu=variable fluorescence signal, ref=constant reference signal, ges=measured total signal;

Figure 5:
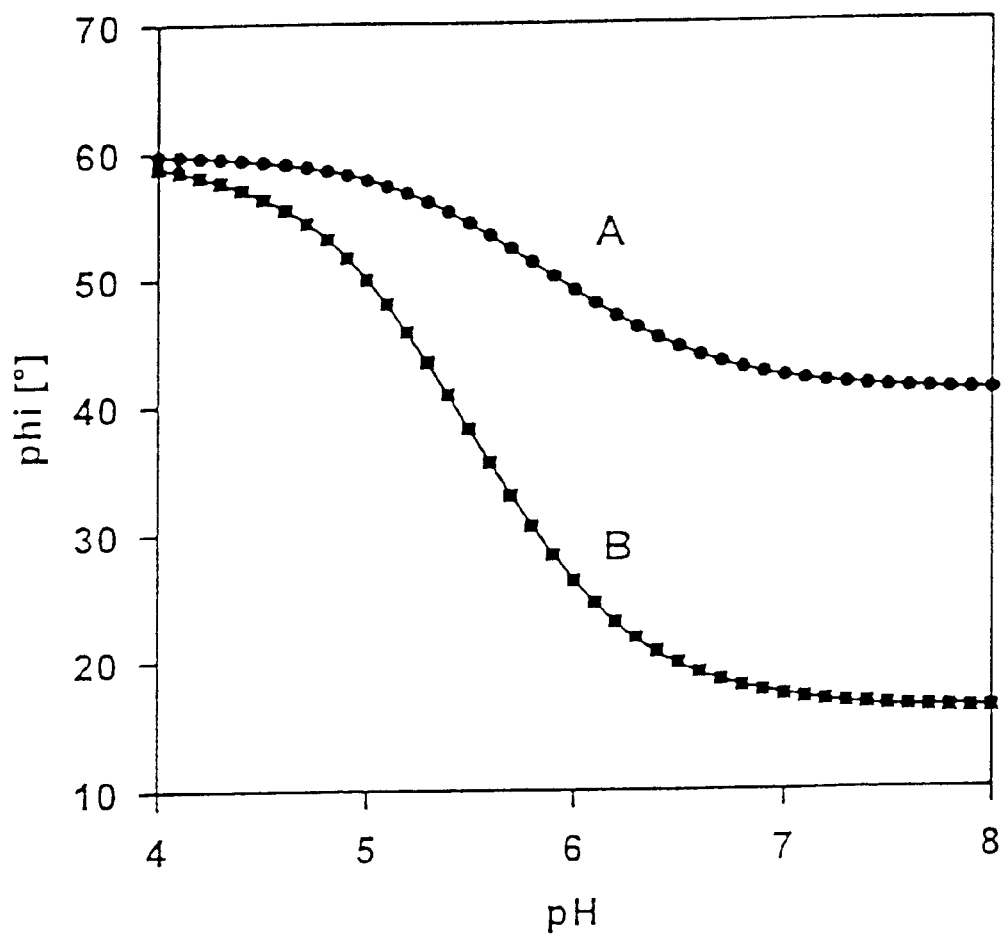
Figure 6:
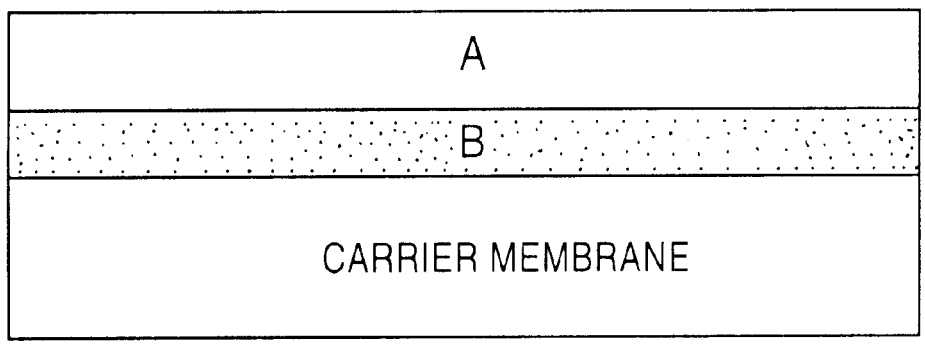
Figure 6:
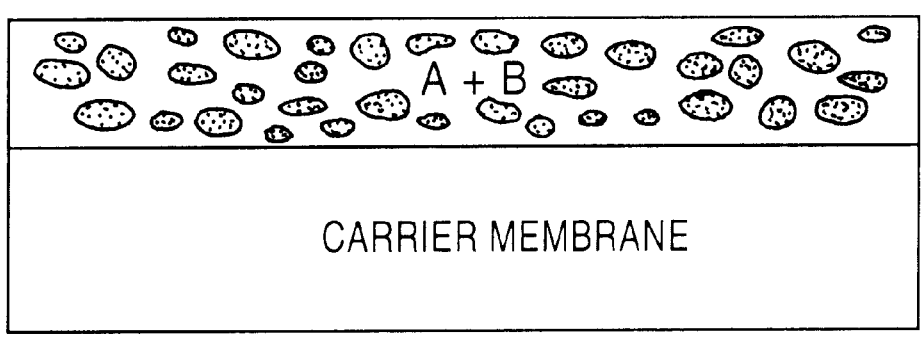
Figure 6:
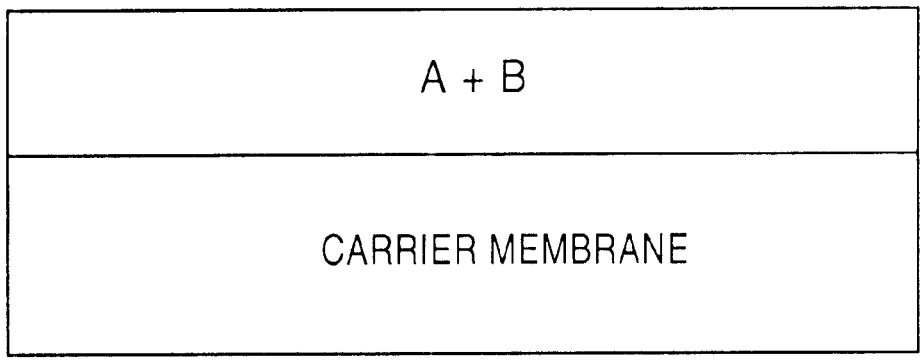
Figure 6:
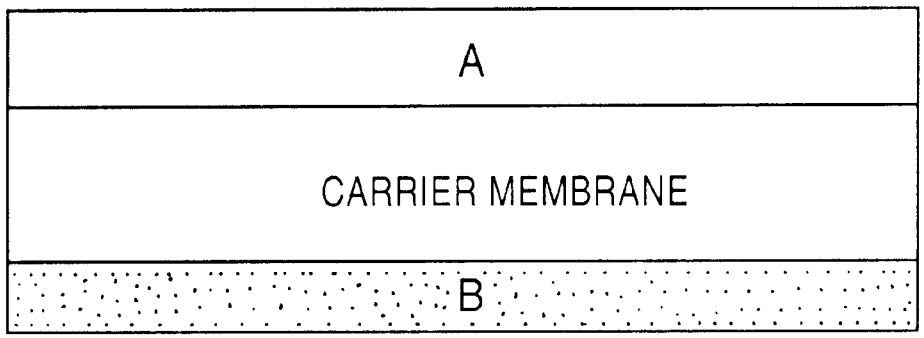

FIG. 5 shows pH calibration curves of a pH sensor according to Example 1 with different amounts of HPTS (A: low HPTS; B: high HPTS), measured as phase shift at a modulation frequency of 80 kHz. A blue LED is used as a light source, and a photodiode as a detector; and FIG. 6 shows four possible combinations of the short-lived, chemically sensitive luminescent material (A) and the inert, long-lived luminescent material (B) in an optical sensor.

Suitable luminescent materials with long decay times, which are inert to the analyte include:

transition metal complexes with ruthenium(II), rhenium (I), or osmium and iridium as central atom and diimine ligands;

phosphorescent porphyrins with platinum, palladium, lutetium or tin as central atom;

phosphorescent complexes of rare earths, such as europium, dysprosium or terbium;

phosphorescent crystals such as ruby, Cr-YAG, alexandrite, or phosphorescent mixed oxides such as magnesium fluoro-germanate.

Suitable short-life fluorescent materials include all dyes whose excitation and emission spectra overlap with the spectra of the long-life luminescent materials referred to above, and whose fluorescence intensity depends on the parameter being monitored.

Examples for potential pairs of luminescent materials or luminophore/fluorophore are:

Ruthenium(II)-(tris-4,7-diphenyl-1,10-phenantroline)/ HPTS

Ruthenium(II)-(tris-4,7-diphenyl-1,10-phenantroline)/ fluorescein

Ruthenium(II)-(tris-4,7-diphenyl-1,10-phenantroline)/ rhodamine B

Ruthenium(II)-(tris-4,7-diphenyl-1,10-phenantroline)/ rhodamine B-octadecyl ester Ruthenium(II)-(tris-4,7-diphenyl-1,10-phenantroline)/ hexadecyl-acridine orange Europium(III)-tris-theonyl-trifluoromethyl acetonate/ hydroxymethyl coumarin Platinum(II)-tetraphenyl porphyrin/rhodamine B-octadecyl ester Platinum(II)-tetraphenyl porphyrin/rhodamine B Platinum(II)-tetraphenyl porphyrin/naphthofluorescein
Platinum(II)-tetraphenyl porphyrin/sulforhodamine 101
Platinum(II)-octaethyl porphyrin/eosin
Platinum(II)-octaethyl porphyrin/thionin
Platinum(II)-octaethyl ketoporphyrin/Nile blue
CR(III)-YAG/Nile blue
Cr(III)-YAG/naphthofluorescein The long-life luminescent material may be integrated into the sensor in different ways (FIG. 6):

- by directly dissolving the luminescent material in the analyte-sensitive layer (FIG. 6, Example 3)
- by incorporation in a polymer which serves as a primer for the sensor layer (FIG. 6, Example 1)
- by incorporation in a polymer which is dispersed in the sensitive layer in micro- or nanoparticles (FIG. 6, Example 2)
- by incorporating luminescent dyes in sol-gel glass, followed by sintering, pulverizing and dispersing the glass in the sensor layer (FIG. 6, Example 2)
- by employing pulverized phosphors which are dispersed in the sensitive layer (FIG. 6, Example 2)
- by coating the outside of a sensor foil, avoiding contact with the sample (FIG. 6, Example 4)
- by covalent or electrostatic-bonding of the fluorescence indicator to the surface of luminescent particles which are either dispersed in a polymer layer or directly distributed in the sample
- by dispersing particles in the sample in which the fluorescence indicator is included as a solute.

If phase modulation techniques are employed at frequencies in the kHz range, it is important to note that it will not be possible to obtain more than a mean phase shift with this type of sensors. Although splitting into both decay time components would be feasible in principle, this would involve considerable instrumentation expense due to the high frequencies required. Due to the strong differences in decay times of the two co-immobilized indicators, time-resolved measurement, which, upon providing an excitation light pulse, is exclusively concerned with the decay characteristic of the luminescence signal after the excitation pulse has been switched off, will often fail to produce a useful parameter, as the short-lived component will decay too quickly and can only be detected at considerable expense.

Figure 4:
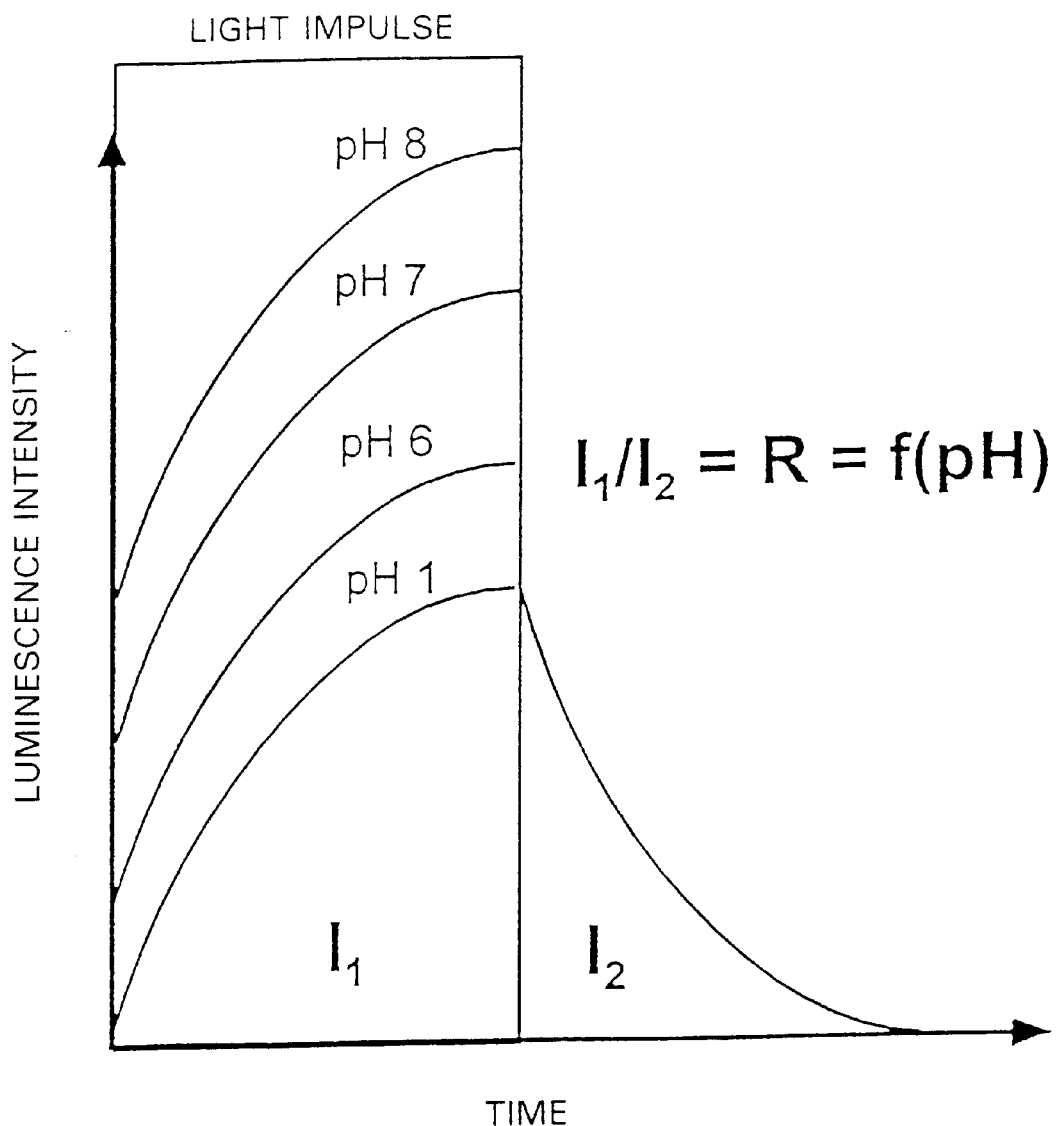
FIG. 4 shows a time-resolved measurement of the ratio of signal intensities during the excitation pulse ($I_1$) and during luminescence decay ($I_2$), the ratio R being independent of the total signal amplitude, as it is only a function of the chemical parameter being monitored.

It is further possible to perform separate time-resolved measurements of signal intensity-during the excitation pulse and in the decay period, and to compute the ratio R of the two signals. As is seen in FIG. 4, this ratio depends solely on the intensity ratio R of the two luminescent components and is completely independent of the total intensity of the signal.

Phase modulation techniques can also be employed to determine the mean phase shift of the luminescence signal. The measuring frequency is adapted to the decay time of the luminescent material and lies between 0.5 and 100 kHz. As is shown below, equation (1) indicates that the measured phase angle $\phi_m$ depends only on the ratio of the two signal intensities but not on the absolute signal level and will hence permit the referencing of the intensity of the short-lived fluorescence component.

Condition 1:
Additive superposition of signals (index ref=reference signal, index flu=fluorescence signal, index m=measured value)

$$A_m \cdot \cos\Phi_m = A_{ref} \cdot \cos\Phi_{ref} + A_{flu} \cdot \cos\Phi_{flu}$$
$$A_m \cdot \sin\Phi_m = A_{ref} \cdot \sin\Phi_{ref} + A_{flu} \cdot \sin\Phi_{flu}$$

Condition 2:
The longer decay time ist significantly greater than the shorter decay time:

$$\tau_{ref} \gg \tau_{flu}$$

If the modulation frequency has been chosen such that it is optimal for $T_{ref}$ i.e., $$\tan\Phi_{ref} = 2\pi \cdot f_{mod} \tau_{ref} = 1$$

one finds for $\Phi_{flu}$:

$$\tan\Phi_{flu} = 2\pi \cdot f_{mod} \cdot \tau_{flu} = \frac{2\pi \cdot \tau_{flu}}{2\pi \cdot \tau_{ref}} = \frac{\tau_{flu}}{\tau_{ref}}$$

Under the above assumption there results for the angle $\phi_{flu}$:

$$\tan\Phi_{flu} = \frac{\tau_{flu}}{\tau_{ref}} \xrightarrow{\tau_{flu} \ll \tau_{ref}} 0 \Rightarrow \Phi_{flu} \to 0$$

Condition 3
The decay time of the dye exhibiting longer decay time is constant for the measurement of interest:

$$\tau_{ref} = constant \Rightarrow \tan\Phi_{ref} = constant \Rightarrow \Phi_{ref} = constant$$

This will simplify the additive equations as follows:

$$A_m \cos\Phi_m = A_{ref} \cos\Phi_{ref} + A_{flu}$$

$$A_m \sin\Phi_m = A_{ref} \sin\Phi_{ref}$$

Dividing the first equation by the second results in:

$$\frac{A_m \cdot \cos\Phi_m}{A_m \cdot \sin\Phi_m} = \cot\Phi_m \qquad (1)$$

$$= \frac{A_{ref} \cdot \cos\Phi_{ref} + A_{flu}}{A_{ref} \cdot \sin\Phi_{ref}} = \frac{A_{ref}}{A_{ref}} \cdot \left(\frac{\cos\Phi_{ref} + A_{flu}/A_{ref}}{\sin\Phi_{ref}}\right)$$

$$\cot\Phi_m = \frac{\cos\Phi_{ref} + A_{flu}/A_{ref}}{\sin\Phi_{ref}} = \cot\Phi_{ref} + \frac{1}{\sin\Phi_{ref}} \cdot A_{flu}/A_{ref}$$

Figure 1B:
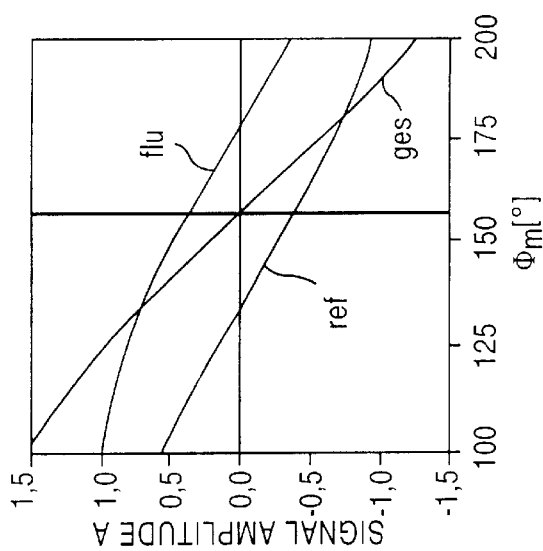
Figure 1D:
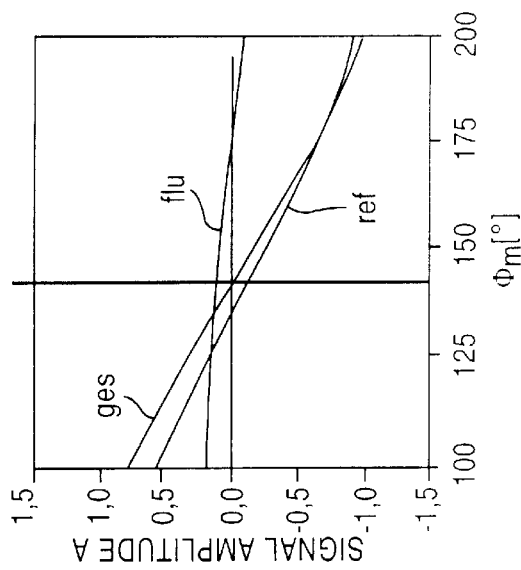
Figure 1A:
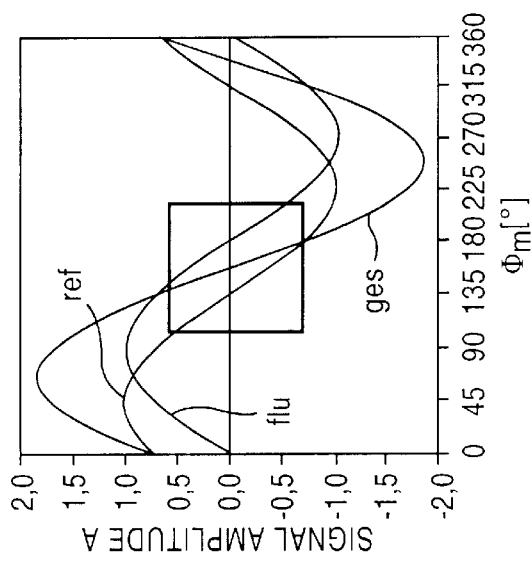
Figure 1C:
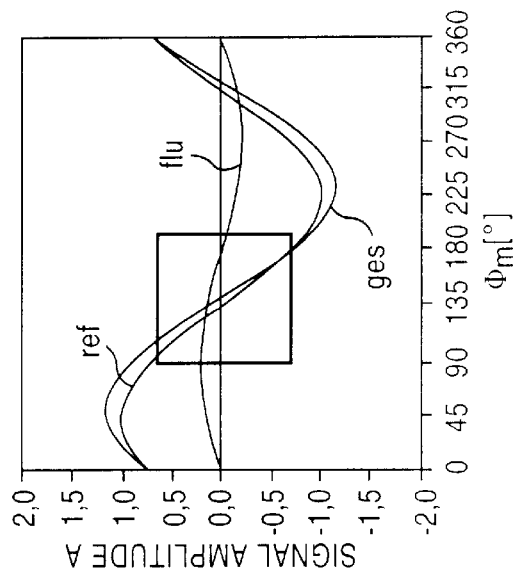
Figure 2:
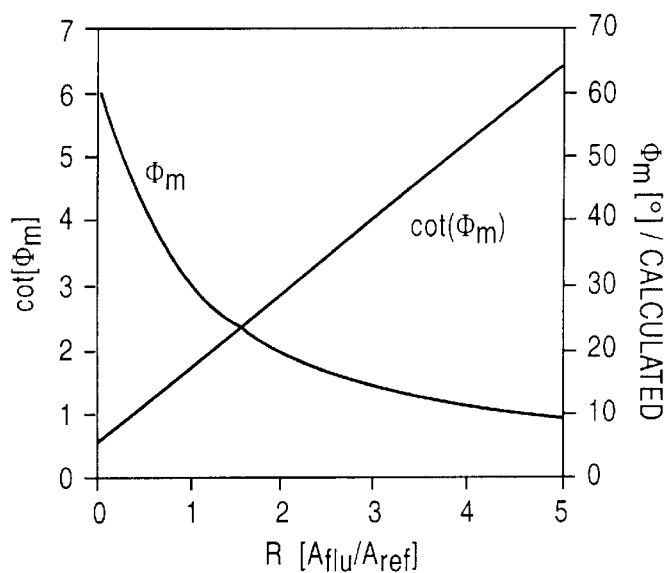
FIG. 2 shows a computed relationship between the measured phase angle $\phi_m$ or its cot ($\phi_m$) and the amplitude ratio R of the two luminescent materials.
Figure 3:
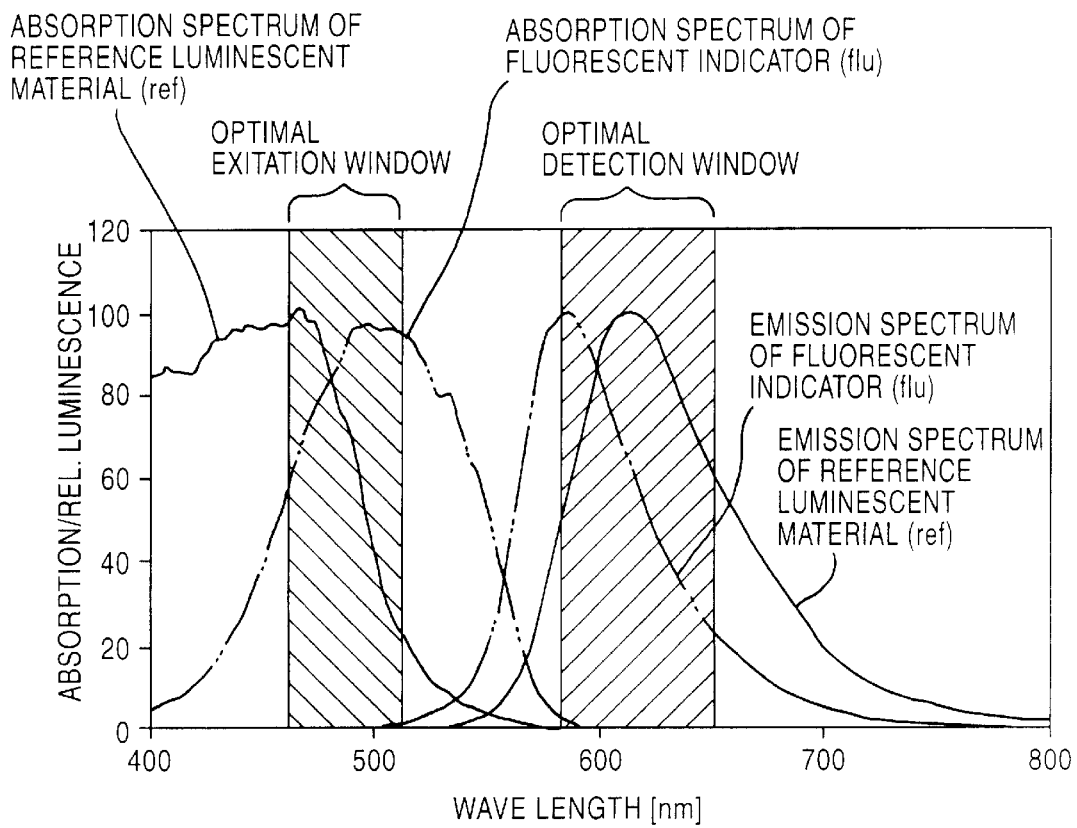
FIG. 3 shows spectral properties of a suitable pair of fluorescence indicator and reference luminescent material. The hatched areas indicate optimum spectral windows for excitation of the luminescence signal and measurement of the emitted light.

Plotting $\phi_m$ against the amplitude ratio thus shows a linear dependence between the cotangent of the measured phase angle $\phi_m$ and the amplitude ratio R (and thus intensity ratio) of the two luminescent materials (cf FIG. 2).

$\cot \phi_m$ represents an intensity ratio without the necessity of separately measuring two signal intensities.

Major advantages are:

Low cost of synthesis and optimization in producing new sensors.

Easy conversion of previously optimized fluorescence sensors to decay time measurement by simple admixture of the long-life luminescent material.

For a set of sensors for a variety of analytes one and the same long-life luminescent material may be employed.

Different sensors may thus be evaluated with the same optoelectronicsystem.

Since the shape of the calibration curve will only depend on the ratio of the two intensities, the sensitivity range of an individual sensor may be optimized simply by varying the amount of luminescent material added.

The same purpose may be achieved by optimum selection of the spectral windows for both excitation and emission.

The cross-sensitivity of long-life luminescence to oxygen may be eliminated by incorporating the indicators into materials that are impermeable to gases.

If phosphorescent solids or glass-embedded luminescent materials are employed, any influence on the signal due to chemical luminescence parameters in the sample will be completely excluded.

Since oxygen cannot quench luminescence no reactive singlet oxygen will be produced in the membrane. As a consequence, photo-decomposition will be reduced and sensor stability improved.

Incorporation of long-life luminescent materials in a glass matrix or as solids will completely prevent leaching. Moreover, their photostability is exceptionally strong.

Whereas in measuring principles based on analyte deactivation of the excited state of the long-life luminescent material (such as PET effect, dynamic quenching, or energy transfer) a decrease in mean decay time will always be accompanied by a decrease in signal intensity, which will impair the signal-to-noise ratio, signal intensity will rise with a decrease in decay time with the type of sensors discussed here. As a consequence, the signal-to-noise ratio will improve significantly over the entire measuring range.

Since the characteristic of these sensors exclusively depends on the ratio of signal components of the two indicators, the following conditions should be met:

1) None of the two indicators should undergo leaching during measurement.
2) The two indicators should not exhibit different rates of photo-decomposition during measurement.
3) The concentration ratio of the two indicators should be maintained constant during membrane fabrication.
4) The decay time of the long-life luminescent material should always be constant.

For many sensors these conditions are easily satisfied.

Examples for optical sensors based on this principle are:

pH Sensor

HPTS adsorbed on cellulose with quaternary ammonium groups and incorporated in poly-hyroxyethylmethacrylate (PHEMA) hydrogel Ru(phen)$_3$Cl$_2$ in sol-gel (sintered, ground, and dispersed in hydrogel). (FIG. 5 shows the calibration curve of this sensor, measured as phase shift at a frequency of 80 kHz.)

pH Sensor

Aminofluorescein covalently attached to sol-gel particles with incorporated Ru(phen)$_3$Cl$_2$ (sintered, ground, and dispersed in hydrogel).

CO$_2$ Sensor

HPTS-CTA$_3$ ionic pair dissolved in ethyl cellulose with tetraoctyl-ammoniumhydroxide as buffer (cf 6)

Ru(4,7-diph-1,10-phen) in PVC as exterior coating of a sensor foil

NH$_3$ Sensor

Rhodamine B dissolved in PVC with NPOE (cf 7)

Pt(II)-tetra-pentafluorophenyl-porphyrin in PVC as exterior coating of a sensor foil Potassium Sensor lipophilized Nile blue dissolved in PVC with plasticizers (cf. 8)

Pt(II)-octaethylketoporphyrin in PVC as exterior coating

The invention thus permits optical monitoring of a chemical, biological or physical parameter of a sample with the use of an optical sensor. The sensor includes two luminescence indicators in co-immobilized form, one of which acts as carrier of a background luminescence signal, which is characterized by long luminescence lifetime (preferably in the range of at least 100 nanoseconds to several milliseconds) and whose intensity and decay time will remain unaffected by the parameter being monitored. The second indicator exhibits shorter-lived fluorescence, preferably in the range of several nanoseconds, which will superpose on the long-lived luminescence signal and whose intensity is a function of the parameter being monitored. With the use of phase modulation techniques or time-resolved measuring methods a reference value is determined, which will represent the ratio of the two individual luminescence intensity components; this reference value is independent of the total intensity of the luminescence signal and will thus permit referencing of the short-lived, analyte-dependent fluorescence component.

References (1) O. S. Wolfbeis, *Fiber Optic Chemical Sensors and Biosensors Vol. II*, CRC press, 1991
(2) S. Draxler, M. E. Lippitsch, *Sens.Actuators* B29, 199, 1995
(3) J. R. Lakowicz, H. Szmacinski, *Sens.Actuators* B11, 133, 1993
(4) J. R. Lakowicz, H. Szmacinski, M. Karakelle,*Anal. Chim.Acta* 272, 179, 1993
(5) J. Sipior, S. Bambot, M. Romauld, G. M. Carter, J. R. Lakowicz, G. Rao, *Anal.Biochem.* 227, 309, 1995
(6) A. Mills, Q. Chang, *Analyst*, 118, 839, 1993
(7) C. Preininger, G. J. Mohr, I. Klimant, O. S. Wolfbeis, *Anal. Chim.Acta*, 334, 113, 1996
(8) U. E. Spichinger, D. Freiner, E. Bakker, T. Rosatzin, W. Simon, *Sens.Actuators* B11, 262, 1993

What is claimed is:

1. Process for optical determination of a biological, chemical or physical parameter of a sample, utilizing at least two different luminescent materials, the first of which being sensitive to the parameter at least with respect to luminescence intensity, and the second of which being insensitive to the parameter at least with respect to luminescence intensity and decay time, and the luminescent materials exhibit different decay times;
the process comprising measuring phase behavior of luminescence responses of both luminescent materials by a single detector and obtaining a reference value being independent of the total intensity of both luminescent materials by the phase behavior measured and determining the parameter utilizing the reference value; wherein a phase shift ($\phi_m$) of the phases of a sum signal of both luminescent materials is used as the reference value.

2. Process according to claim 1, characterized in that the decay time of the second luminescent material is longer than that of the first luminescent material.

3. Process according to claim 1, characterized in that excitation- and/or emission spectra of the luminescent materials are mutually overlapping.

4. Process according to claim 1, characterized in that the luminescent materials are jointly excited by a single light source.

5. Process according to claim 1, characterized in that the luminescent materials are excited simultaneously.

6. Process according to claim 1, characterized in that the reference value is determined from a sum signal of the resulting joint luminescence response.

7. Process according to claim 1, characterized in that as reference value a ratio of both intensities l1 and l2 in a course of time is utilized, whereby l1 means measured intensity of light emitted by both luminescent materials in a course of time during which a light source is on, and l2 means measured intensity of light emitted by reference dye in a course of time after the light source has been switched off.

8. Process according to claim 1, characterized in that short-life luminescent material is fixed at a surface of particles containing long-life luminescent material and that the particles are added to the sample directly without any additional carrier.

9. Process according to claim 1, characterized in that the chemical parameter to be measured in the sample is pH-value, concentrations of certain different ionic compounds or the concentrations of gaseous components or the redox potential.

10. Process according to claim 1, characterized in that the biological parameter to be measured is concentration of an antibody or antigen marked with fluorescent dyes.

11. Process for optical determination of a biological, chemical or physical parameter of a sample, utilizing at least two different luminescent materials, the first of which being sensitive to the parameter at least with respect to luminescence intensity, and the second of which being insensitive to the parameter at least with respect to luminescence intensity and decay time, and the luminescent materials exhibit different decay times; the process comprising measuring time behavior of a sum signal of luminescence responses of both luminescent materials during an excitation pulse and during the decay period by a single detector and obtaining a reference value being independent of total intensity of both luminescent materials by the time behavior measured and determining the parameter utilizing the reference value; wherein the intensity ratio $l_1/l_2$ of the sum signal of both luminescent materials is used as the reference value and wherein $l_1$ is the luminescence intensity during excitation and $l_2$ is the luminescence intensity during decay.

12. The process for optical determination of claim 1 wherein the optical determination is luminescence determination of a biological, chemical or physical parameter of a sample.

13. Process according to claim 5, characterized in that the luminescent materials are excited simultaneously with simultaneous start of excitation and equal duration of excitation.

14. Process according to claim 9, characterized in that the chemical parameter to be measured in the sample is pH-value, concentrations of certain different ionic compounds of potassium, calcium, nitrate, chloride or different heavy metals or concentrations of gaseous $CO_2$ or $NH_2$ components or redox potential.

* * * * *